(12) United States Patent
Alkanhal

(10) Patent No.: US 8,419,944 B2
(45) Date of Patent: Apr. 16, 2013

(54) CONTINUOUS AMBULATORY HEMOFILTRATION DEVICE

(76) Inventor: Fahad Ahmed Alkanhal, Beijing (CN)

( * ) Notice: Subject to any disclaimer, the term of this patent is extended or adjusted under 35 U.S.C. 154(b) by 423 days.

(21) Appl. No.: 12/587,021

(22) Filed: Oct. 1, 2009

(65) Prior Publication Data

US 2011/0282262 A1  Nov. 17, 2011

(51) Int. Cl.
*B01D 11/00* (2006.01)
*B01D 61/00* (2006.01)
*A61M 37/00* (2006.01)
*C02F 1/44* (2006.01)

(52) U.S. Cl.
USPC ......... 210/646; 604/6.09; 604/6.11; 604/6.14

(58) Field of Classification Search .................. 604/4.01, 604/5.01, 6.01, 6.1, 6.11, 6.13–6.16; 210/645–647
See application file for complete search history.

*Primary Examiner* — Melanie Hand
(74) *Attorney, Agent, or Firm* — John Alumit

(57) ABSTRACT

A Continuous Ambulatory Hemofilter includes an outer casing, multifunction pump, hemofilter, reverse osmosis filter, power source, drainage bag, blood lines and fluid lines, characterized in that the hemofiltrate from the hemofilter is moved to a reverse osmosis filter. The ultrafiltrate fluid from the reverse osmosis filter flows to the out-flow tube of the hemofilter vein line through a dedicated fluid line. The exit of the reverse osmosis filter is connected to a drainage bag. The multifunction pump moves blood from a permanent jugular catheter to the hemofilter, and fluids between the hemofilter, reverse osmosis filter, vein line and drainage bag. An electrode is placed at the in-flow tube of the hemofilter to measure incoming blood osmolality. The electrode is connected to a microprocessor that is further connected to a computer-controlled valve at the out-flow line of the reverse osmosis filter. The microprocessor is connected with a memory card.

15 Claims, 3 Drawing Sheets

CONTINUOUS AMBULATORY HEMOFILTRATION DEVICE

CROSS-REFERENCE TO RELATED APPLICATION

This application claims the benefit of the priority filing date in PCT/CN2007/002663 referenced in WIPO Publication WO 2008/104108. The earliest priority date claimed is Feb. 28, 2007.

FEDERALLY SPONSORED RESEARCH

Not Applicable

SEQUENCE LISTING OR PROGRAM

Not Applicable

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file, or records, but otherwise reserves all copyright rights whatsoever.

BACKGROUND

1. Technical Field

This invention relates to a medical apparatus, particularly a Continuous Ambulatory Hemofiltration Device.

2. Technical Background

The kidney has many vital functions which include removal of excessive water and electrolytes and removal of metabolic waste products. When the kidney fails to perform its functions, a patient will die unless he receives renal replacement therapy. The currently available renal replacement therapies are the following:

Renal transplantation. A shortage of graft kidneys makes this option limited. In addition, patients must be placed on expensive immunosuppressive medications that have a lot of many side effects, and patients must be regularly monitored. There are many contraindication of renal transplantation.

Peritoneal dialysis. This requires a large quantity of expensive fluids and other disposable materials. In addition, peritoneal dialysis has many complications, and the efficiency of the peritoneal membrane decreases markedly with time. This type of renal replacement therapy requires daily effort from the patient for fluid exchange.

Conventional hemodialysis. Large numbers of end stage renal failure patients receive conventional hemodialysis which requires a large number of nursing staff, and a lot of expensive fluids and disposables. In addition, patients must come to the hemodialysis unit about 3 times per week and be injected with two large needles in each hemodialysis session. Furthermore, this type of therapy has a lot of complications. In hemodialysis units, conventional hemofiltration can be performed but require even more expensive fluids and disposables.

DESCRIPTION OF THE INVENTION

The present invention decreases the medical care cost, inconvenience and agony of renal failure patients. The object of the present invention is to provide a small-sized, ambulatory hemofiltration device that can independently produce hemofiltration replacement solution.

The technical scheme to achieve the invention is as follows: A Continuous Ambulatory Hemofiltration (CAHF) Device, consisting of an outer casing, a multifunction pump, a hemofilter, a reversed osmosis filter, a power source, a drainage bag, blood lines and fluid lines, characterized in that blood moves from a patient to a hemofilter, then the hemofiltrate produced therein is moved to a reverse osmosis filter.

The ultrafiltrate fluid from the reverse osmosis filter flows to the out-flow tube of the hemofilter vein line through a specific fluid line. The exit of the reverse osmosis filter is connected to a drainage bag. The role of the a multifunction pump is to move the blood from a permanent jugular catheter to the hemofilter, and to move fluids between the hemofilter, the reverse osmosis filter, the vein line and the drainage bag. An electrode is placed at the in-flow tube of the hemofilter to measure the incoming blood osmolality. The electrode is connected to a microprocessor that is further connected to a computer-controlled valve that is placed at the out-flow line of the reverse osmosis filter. The microprocessor is connected with a memory card, The in-flow line to the reversed osmosis filter, the out-flow line of the reverse osmosis filter, and the ultrafiltrate line from the reverse osmosis filter, are connected to a volumetric device to measure the volumes of fluids going through, those lines. The volumetric device is connected with the microprocessor that is connected to the memory card.

The power source is in the form of two rechargeable batteries connected in parallel. The multifunctional pump is a coaxial (axle-sharing) multifunctional pump. There are two impellers driven by one micro electric motor. The one impeller impels the blood from the patient's body to the hemofilter, and the hemofiltrate from the hemofilter to the reverse osmosis filter. The other impeller impels the ultrafiltrate (product fluid) from the reverse osmosis filter to the tube connected with a patient's vein.

The hemofilter and the reversed osmosis filter are placed in tunnels at either side of the casing, and other parts are placed in the center between the two tunnels. There are two power indicating alarms on the outer casing of the device. One indicates low blood flow through the hemofilter and the other one indicates low battery power. There is a binding belt on the outer casing. A valve is placed at the fluid line that connects the reverse osmosis filter and the inlet of hemofilter. A Valve is placed at the fluid line that connects the reverse osmosis filter and hemofilter itself. The branch of the fluid line carrying the dialysate to the hemofilter itself must enter to the hemofilter through the upper end of one side of the hemofilter to the dialysate compartment.

A store of mixed powder of sodium chloride and sodium bicarbonate is provided to add enough sodium chloride or bicarbonate to the ultrafiltrate from the reverse osmosis filter. Part of the ultrafiltrate from the reverse osmosis filter will go through cartilage houses, through small branch tube lines with a one-way valve, toward the cartilage houses.

There are electrodes to measure the sodium concentration in the fluid coming from each cartilage house before it reenters the main line going to the hemofilter. There are control valves on the exit of each micro cartilage house. The sodium concentration measurements will be transmitted to the electronic microprocessor which will send information to the memory card and to the pre-programmed electronic card, which will then adjust the amount of fluid coming from the cartilage houses through the control valves.

There are replacement microcartilages. One contains sodium bicarbonate powder and another contains powder of the other required electrolytes, including, calcium, potassium, and sodium chloride. Each one of these microcartilages will be fixed to one of the cartilage houses.

The present device, having a simple and portable structure, can be easily bound to a patient's body. When the power-indicating alarm is activated, one of the batteries can be replaced without affecting the continuous operation of the device as the two batteries are connected in parallel form. If the blood flow alarm light turns on it indicates a failure of a device, function and the patient must go to the hospital immediately. The hemofiltrate from the hemofilter is then moved to a reverse osmosis filter. The ultrafiltrate from the reverse osmosis filter flows back to a patient's body as replacement solution. This greatly reduces the medical care cost of a patient.

SUMMARY

The present invention decreases the medic care cost, inconvenience and agony of renal failure in patients. The object of the invention is to provide a small-sized, ambulatory hemofiltration device that can produce hemofiltration replacement solution itself.

The invention is a Continuous Ambulatory Hemofiltration (CAHF) Device consisting of an outer casing, a multifunction pump, a hemofilter, a reverse osmosis filter, a power source, a drainage bag, blood lines and fluid lines, characterized in that the hemofiltrate from the hemofilter is moved to a reverse osmosis filter; ultrafiltrate fluid from the reversed osmosis filter flows to the out-flow tube of the hemofilter vein line through a specific fluid line; the exit of the reverse osmosis filter is connected to a drainage bag; the multifunction pump moves blood from a permanent jugular catheter to the hemofilter, and moves fluids between the hemofilter, reverse osmosis filter, vein line and drainage bag; an electrode placed at the inflow tube of the hemofilter measures the incoming blood osmolality, the electrode is connected to a microprocessor that is further connected to a computer-controlled valve placed at the out-flow line of the reverse osmosis filter; and the microprocessor is connected to a memory card.

The present device, having a simple and portable structure, can be easily bound to a patient's body. When the power-indicating alarm is activated, one of the batteries can be replaced without affecting the continuous operation of the device as the two batteries are connected in parallel. If the blood flow alarm light turns on, it indicates a failure of the device and the patient must go to the hospital immediately. The hemofiltrate from the hemofilter is then moved to a reverse osmosis filter. The ultrafiltrate from the reverse osmosis filter flows back to a patient's body as replacement solution. This greatly reduces the medical care cost of a patient.

DESCRIPTION

Figure 1:
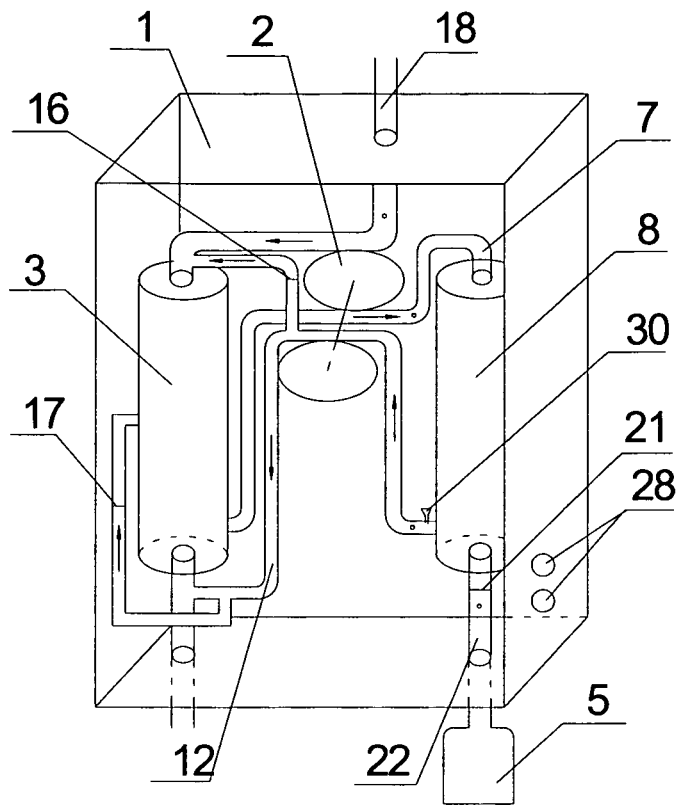
FIG. 1 is a structural view of the inside of the device.
Figure 2:
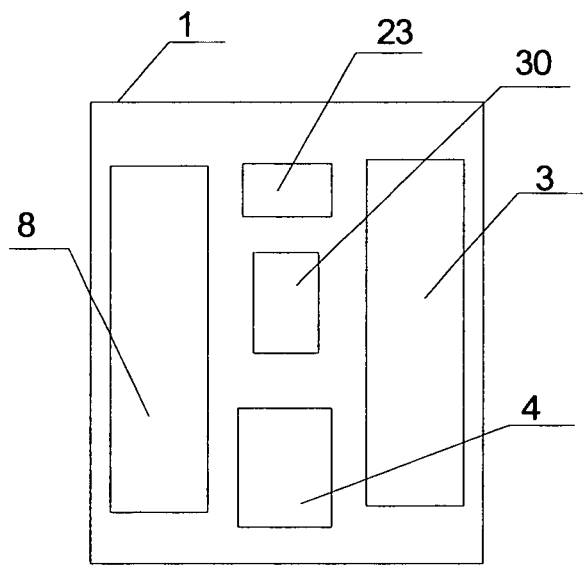
FIG. 2 is an illustrative view of the back of the device.
Figure 3:
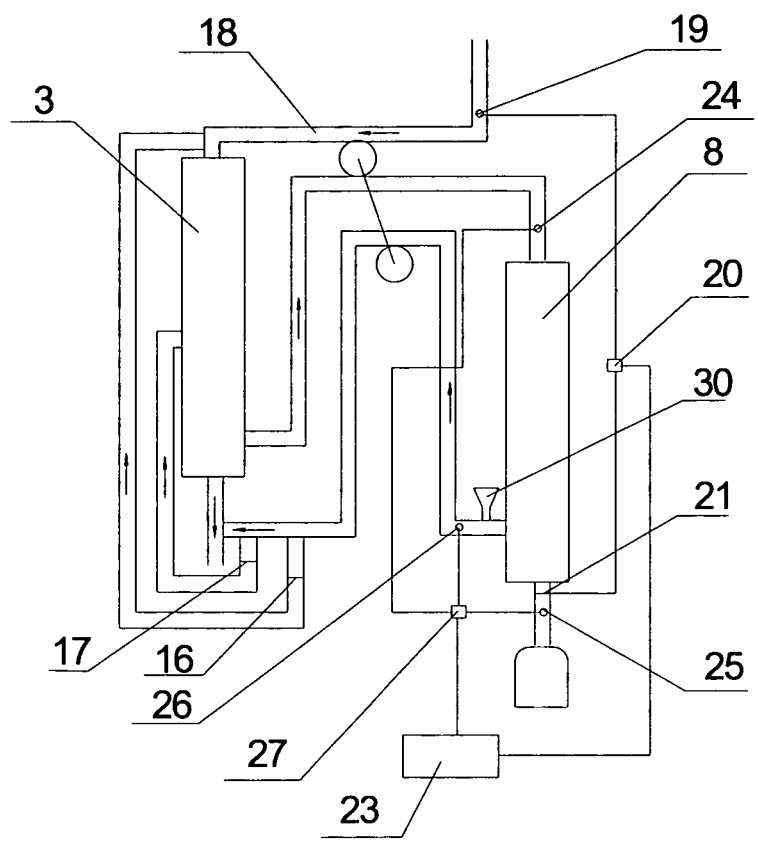
FIG. 3 is an illustrative view of the connection of major parts of the device.

As shown in FIGS. 1 and 2, the Continuous Ambulatory Hemofiltration (CAHF) Device consists of an, outer casing (1), a multifunction pump (2), a hemofilter (3), a power source (4), a drainage bag (5), and blood lines and fluid lines. The hemofiltrate from the hemofilter (3) is moved to a reverse osmosis filter (8) through a fluid line (7). The exit of the reverse osmosis filter (8) is connected to a drainage bag (5). The ultrafiltrate from the reverse osmosis filter (8) is connected to the inlet, the exit of hemofilter (3), and to the hemofilter (3) itself via a fluid line (12), respectively. Valves (16 and 17) are placed at the fluid lines that connect the reversed osmosis filter (8) and the inlet of the hemofilter (3), and the hemofilter (3) itself, respectively. The branch of the fluid line carrying the dialysate to the hemofilter (3) itself must enter to the hemofilter (3) through the upper end of one side of the hemofilter (3) to the dialysate compartment. The multifunction pump (2) moves the blood from a permanent jugular catheter (18) to the hemofilter (3), and moves fluids between the hemofilter (3), the reversed osmosis filter (8), the fluid line (12), and the drainage bag (5).

The multifunction pump (2) has two impellers driven by one micro electric motor. One impeller impels the blood from the patient's body to the hemofilter (3), and the hemofiltrate from the hemofilter (3) to the reverse osmosis filter (8). The other impeller impels the ultrafiltrate (product fluid) from the reverse osmosis filter (8) to the tube connected with the fluid line (12). An electrode (19) is placed at the inflow tube of the hemofilter (3) to measure the incoming blood osmolality. The electrode (19) is connected to a microprocessor (20) that is further connected to a computer-controlled valve (21) that is placed at the out-flow line of the reverse osmosis filter (8). The microprocessor is connected with a memory card (23). Electrodes (24, 25 and 26) are placed at the inlet, exit and out-flow line of the ultrafiltrate of the reverse osmosis filter (8), respectively. The three electrodes are connected to volumetric devices to measure fluids going through those lines. The volumetric devices are connected with a microprocessor (27) to send that information to a memory card (23). The power source (4) is composed of two rechargeable batteries connected in parallel form. The hemofilter (3) and the reverse osmosis filter (8) are placed in tunnels at either side of the casing, and other parts are placed in the center between the two tunnels.

Two illuminated alarms (28) are placed on the outer casing (1). One indicates low blood flow through the hemofilter, and the other one indicates low battery power. A binding belt (29) is mounted on the outer casing (1). A store of mixed powder of sodium chloride and sodium bicarbonate (30) is provided to add enough sodium chloride or bicarbonate to the ultrafiltrate from the reverse osmosis filter (8).

In order to make this invention better understood, the working process of the device is concisely described hereunder. Blood flows from a permanent jugular catheter to the hemofilter. The purified blood flows back to the patient's body. The hemofiltrate is moved to the reverse osmosis filter. The rejected fluid from the reverse osmosis filter flows to the drainage bag, while the ultrafiltrate flows back to the patient's body as replacement solution. To avoid clotting in the hemofilter, part of the ultrafiltrate (20-30%) from the reverse osmosis filter must be connected to incoming blood through the hemofilter. Part of the ultrafiltrate can also be connected to the hemofilter itself as dialysate. The percentage of ultrafiltrate to the inlet of the hemofilter, or to the hemofilter itself, can be adjusted by a doctor by adjusting the valves on the lines going to these sites. An electrode is placed at the inflow tube of the hemofilter to measure the incoming blood osmolality. The electrode feedbacks the measurement to a microprocessor that controls the operation of a valve being placed at the out-flow line of the reverse osmosis filter, and thereby controls the volume of fluid flowing into the patient's body according to the patient's blood osmolality. All relevant information is stored in the memory card. Electrodes (24, 25 and 26) are placed at the inlet, exit and out-flow line of the ultrafiltrate of the reverse osmosis filter, respectively. The three electrodes are connected with a volumetric device and with a microprocessor (27) that stores information in memory card (23) regarding the amount of fluids going in and out of the reverse osmosis filter. In this way, a patient need not see a doctor frequently, and he/she only needs to see a doctor once a month to have his/her status monitored by a doctor who checks the information in the memory card, using a computer. If needed, part of the ultrafiltrate from the reverse osmosis filter can go through cartilage houses 35 and 38, as seen in FIG. 4, through small branch tube lines with a one-way valve pointing toward the cartilage houses.

Figure 4:
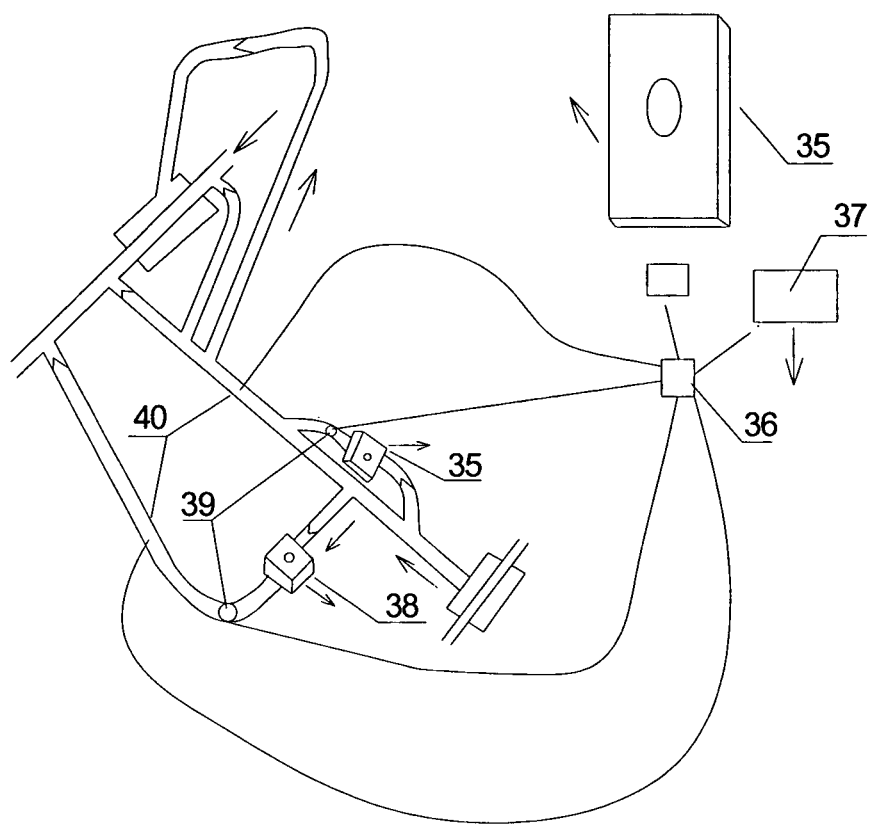
FIG. 4 is an illustrative view of the cartilage houses.
Figure 5:
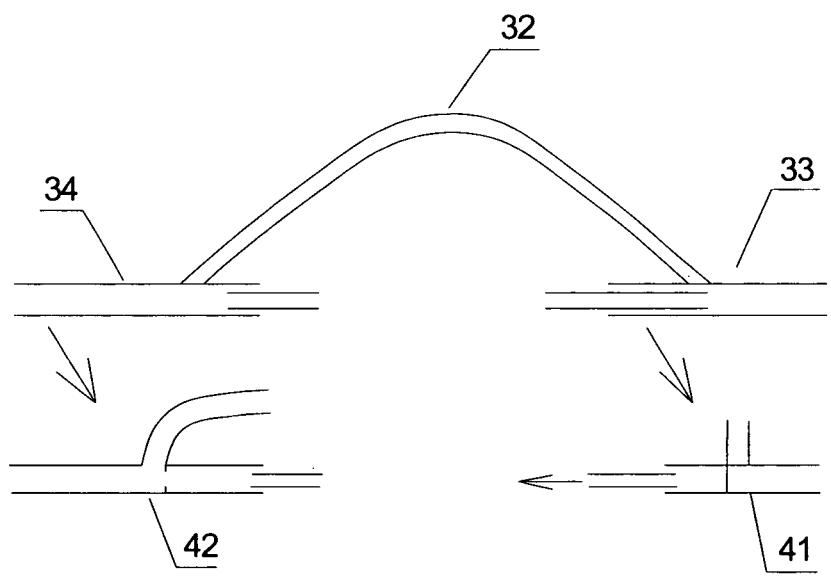
FIG. 5 is an illustrative view of the connecting scheme between the device and a patient's arteries and veins.

There are electrodes to measure the sodium concentration in the fluid coming from each cartilage house before it reenters the main line going to the hemofilter [No. 40 in FIG. 4]. There are control valves on the exit of each micro cartilage house [no. 39 in FIG. 4]. The sodium concentration measurements goes to an electronic microprocessor which will send information to the memory card and to the programmed electronic card. Then the electronic microprocessor will adjust the amount of fluid coming from the cartilage houses through the contrail valves 39. There are replacement microcartilages [no. 36 in FIG. 4]. One contains sodium bicarbonate powder and the other contains powder of the other required electrolytes, including, calcium, potassium, and sodium chloride. Each of these microcartilages are fixed to one of the cartilage houses. The device is fixed to the right side of the chest of the patient, or other adequate place, by a binding belt where it can be connected to a right-sided permanent jugular catheter. In addition, the device can be connected to an artery [no. 33 in FIG. 5] and vein [no. 34 in FIG. 5]. In the event the device is pulled out accidently, both artery and vein will be closed by pulled flaps. The flaps will be pulled away from the opening of the bypass tube [no. 32 in FIG. 5] because, during accidental pulling of the device, the connecting piece of the device will pull the flaps closed. This mechanism is designed to avoid bleeding in the event of an accidental pulling of the device.

What is claimed is:

1. A Continuous Ambulatory Hemofiltration (CAHF) Device comprising:
   an outer casing, a multi-function pump, a hemofilter, a reverse osmosis filter, a power source, a drainage bag, and fluid lines;
   wherein the hemofiltrate from the hemofilter is moved to a reverse osmosis filter;
   wherein ultrafiltrate fluid from the reverse osmosis filter flows to the out-flow tube of a hemofilter vein line through a dedicated fluid line;
   wherein the exit of the reverse osmosis filter is connected to a drainage bag;
   wherein the multi-function pump moves blood from a permanent jugular catheter to the hemofilter, and moves fluids between the hemofilter, reverse osmosis filter, vein line and drainage bag;
   wherein an electrode placed at the in-flow tube of the hemofilter measures incoming blood osmolality, the electrode being connected to a microprocessor that is further connected to a computer-controlled valve placed at the out-flow line of the reverse osmosis filter, and the microprocessor being connected to a memory card.

2. The Continuous Ambulatory Hemofiltration Device according to claim 1, characterized in that the in-flow line to the reverse osmosis filter, the out-flow line from the reverse osmosis filter, and an ultrafiltrate line from the reverse osmosis filter are connected to a volumetric device to measure the volumes of fluids going through those lines, the volumetric device being connected to the microprocessor that is connected to the memory card.

3. The Continuous Ambulatory Hemofiltration Device according to claim 1, characterized in that the power source is in the form of two rechargeable batteries that are connected in parallel.

4. The Continuous Ambulatory Hemofiltration Device according to claim 2, characterized in that the power source is in the form of two rechargeable batteries that are connected in parallel.

5. The Continuous Ambulatory Hemofiltration Device according to claim 1, characterized in that the multifunctional pump is coaxial (axle-sharing) with at least two impellers driven by at least one micro electric motor, one impeller impels the blood from the patient's body to the hemofilter and impels the hemofiltrate from the hemofilter to the reverse osmosis filter, and the other impeller impels the ultrafiltrate from the reverse osmosis filter to the tube connected with a patient's vein.

6. The Continuous Ambulatory Hemofiltration Device according to claim 2, characterized in that the multifunctional pump is coaxial (axle-sharing) with at least two impellers driven by at least one micro electric motor, one impeller impels the blood from the patient's body to the hemofilter, and impels the hemofiltrate from the hemofilter to the reverse osmosis filter, and the other impeller impels the ultrafiltrate from the reverse osmosis filter to the tube connected with a patient's vein.

7. The Continuous Ambulatory Hemofiltration Device according to claim 1, characterized in that the hemofilter and the reverse osmosis filter are placed in tunnels at either side of the outer casing, and other parts are placed in the center between the two tunnels.

8. The Continuous Ambulatory Hemofiltration Device according to claim 1, characterized in that the device is fixed to the right side of the chest of a patient by a binding belt where it is connected to a right-side permanent jugular catheter, the device being connected with an artery and vein, and connecting pieces of the device cause both artery and vein to close by pulling flaps away from the opening of a bypass tube so that the blood will go directly from the artery to the vein through the bypass tube to avoid bleeding if pulled out accidentally.

9. The Continuous Ambulatory Hemofiltration Device according to claim 1, characterized in that 20% to 30% of the ultrafiltrate from the reverse osmosis filter can be connected to incoming blood through the hemofilter to dilute the blood and avoid clotting in the hemofilter.

10. The Continuous Ambulatory Hemofiltration Device according to claim 1, characterized in that the ultrafiltrate fluid from the reverse osmosis filter can be used as a dialysate to perform dialysis or hemodiafiltration, given that the fluid line carrying the dialysate to the hemofilter enters the hemofilter through the upper end of one side of the hemofilter to a dialysate compartment.

11. The Continuous Ambulatory Hemofiltration Device according to claim 1, characterized in that a store of mixed powder of sodium chloride and sodium biacarbonate is provided to add sodium chloride or biacarbonate to the ultrafiltrate from the reverse osmosis filter as needed.

12. A Continuous Ambulatory Hemofiltration (CAHF) Device comprising:

an outer casing, a multifunction pump, a hemofilter, a reverse osmosis filter, a power source, a drainage bag, blood lines and fluid lines, at least two replaceable microcartilage, and at least one cartilage house;

wherein the hemofiltrate from the hemofilter is moved to a reversed osmosis filter; ultrafiltrate fluid from the reversed osmosis filter flows to the out-flow tube of the hemofilter vein line through a specific fluid line; the exit of the reversed osmosis filter is connected to a drainage bag; the multifunction pump moves blood from a permanent jugular catheter to the hemofilter, and moves fluids between the hemofilter, reverse osmosis filter, vein line and drainage bag; an electrode placed at the in-flow tube of the hemofilter measures the incoming blood osmolality;

wherein the electrode being connected to a microprocessor that is further connected to a computer-controlled valve placed at the out-flow line of the reverse osmosis filter, the microprocessor being connected to a memory card; and the at least two replaceable microcartilages, one containing sodium bicarbonate powder and the other containing other needed electrolyte powder including calcium, potassium and sodium chloride, are fixed on a corresponding cartilage house where part of the ultrafiltrate from the reverse osmosis filter can pass through and mix with those electrolytes before mixing again with the main stream of ultrafiltrate going back to the blood and returning to the body.

13. The Continuous Ambulatory Hemofiltration Device according to claim 12, wherein the electrodes connected to the microprocessor measuring sodium concentrations are fixed on small tube branches returning the ultrafiltrate after it mixes with the electrolytes going back to the main stream ultrafiltrate returning to the blood.

14. The Continuous Ambulatory Hemofiltration Device according to claim 12, wherein the microprocessor controls valves fixed on the exits of the cartilage houses so that the right concentrations of the electrolytes in the ultrafiltrate going back to the blood is assured.

15. The Continuous Ambulatory Hemofiltration Device according to claim 1, wherein the outer casing of the device comprises at least two light alarms, one indicating low blood flow in the device and the other indicating low battery power.

* * * * *